(12) United States Patent
Shibata

(10) Patent No.: US 7,906,073 B2
(45) Date of Patent: Mar. 15, 2011

(54) ANALYZERS AND METHODS FOR ANALYZING ANALYTES

(75) Inventor: Masaharu Shibata, Kobe (JP)

(73) Assignee: Sysmex Corporation, Kobe (JP)

( * ) Notice: Subject to any disclaimer, the term of this patent is extended or adjusted under 35 U.S.C. 154(b) by 1104 days.

(21) Appl. No.: 10/611,236

(22) Filed: Jun. 30, 2003

(65) Prior Publication Data

US 2004/0023404 A1 Feb. 5, 2004

(30) Foreign Application Priority Data

Jul. 1, 2002 (JP) .................................. 2002-192293

(51) Int. Cl.
*G01N 7/00* (2006.01)
(52) U.S. Cl. ............. 422/83; 422/88; 422/89; 73/23.22; 73/23.35; 73/23.36; 73/23.41
(58) Field of Classification Search .................... 422/83, 422/88, 89; 436/147, 161; 73/23.21, 23.22, 73/23.25, 23.35, 23.36, 23.41
See application file for complete search history.

(56) References Cited

U.S. PATENT DOCUMENTS

| 4,070,155 | A | * | 1/1978 | Fraim | ............................ 436/114 |
| 5,387,334 | A | | 2/1995 | Kuroda et al. | |
| 5,413,938 | A | | 5/1995 | Tsujino et al. | |
| 5,665,314 | A | * | 9/1997 | Berger et al. | .................... 422/89 |
| 5,830,353 | A | * | 11/1998 | Henderson | ................. 210/198.2 |
| 5,830,701 | A | | 11/1998 | Houwen et al. | |
| 5,939,326 | A | | 8/1999 | Chupp et al. | |
| 6,530,260 | B1 | * | 3/2003 | Mustacich et al. | ........... 73/23.41 |
| 6,534,136 | B2 | * | 3/2003 | Weder | ........................... 428/34.1 |
| 6,846,458 | B1 | * | 1/2005 | Staphanos | ........................ 422/81 |
| 2002/0034824 | A1 | | 3/2002 | Abo | |

FOREIGN PATENT DOCUMENTS

| EP | 1 189 059 A1 | 3/2002 |
| JP | 54-161389 A | 12/1979 |
| JP | 1-305361 A | 12/1989 |
| JP | 6-266448 A | 9/1994 |

OTHER PUBLICATIONS

Peng, L., et al, "Determination of Peripheral Blood Stem Cells by the Sysmex SE-9500" *Clin. Lab. Haem*, vol. 23, 2001, pp. 231-236.

* cited by examiner

*Primary Examiner* — Lyle A Alexander
*Assistant Examiner* — Dwayne K Handy
(74) *Attorney, Agent, or Firm* — Brinks Hofer Gilson & Lione

(57) ABSTRACT

Analyzers are described that contain a detector for detecting a signal from an analyte; a heater for heating a fluid; a fluid supplier for supplying the fluid heated by the heater to the detector; and a controller for controlling the detector, the heater, and the fluid supplier. Methods for analyzing analytes are also described.

22 Claims, 9 Drawing Sheets

ANALYZERS AND METHODS FOR ANALYZING ANALYTES

RELATED APPLICATIONS

This application claims priority under 35 U.S.C. §119 to Japanese Patent Application No. 2002-192293, filed Jul. 1, 2002.

FIELD OF THE INVENTION

The present invention relates to sample analyzers and analyzing methods. More specifically, the present invention relates to samples analyzers and analyzing methods whereby analysis results are responsively influenced by the reaction temperature with the reagent solution. The present invention further relates to sample analyzers and analyzing methods capable of providing an optimum temperature for analyzing a sample.

BACKGROUND

Samples of blood and urine contain constituent components that are difficult to analyze directly in minute quantities. When analyzing such components, a sample is generally diluted with a reagent solution, and analysis is performed after the sample and reagent have reacted. However, depending on the sample, the progress of the reaction between the sample and the reagent may be greatly affected by conditions such as temperature, sunlight, humidity and the like, such that there may be wide variation in the results obtained from the same sample depending on conditions.

For example, when analyzing peripheral blood stem cells (PBSC) in the blood, the analysis results obtained may vary greatly if there is a slight change in temperature.

Methods of transplanting stem cells (bone marrow transplants), which are the origin of blood cells, are used as treatments for leukemia. When using methods of transplanting hepatic cells, it is important to accurately know the number of peripheral blood stem cells (PBSC). It is particularly important to accurately know the number of PBSC for peripheral blood stem cell transplantation (PBSCT), which has become widespread in recent years as a method of transplanting hepatic cells.

PBSCT is typically performed as follows. First, the patient is administered a normal dose of chemical agent, which reduces the number of leukocytes in the peripheral blood. The leukocytes begin to increase 5 to 7 days later. It is during this period that the number of PBSC increases in the peripheral blood.

When the number of PBSC in the peripheral blood has sufficiently increased (5 to 20 days), PBSC are collected by a blood component separator, and the PBSC are frozen and stored. When collecting the PBSC, it is important to accurately know the number of PBSC in the peripheral blood. In order to collect an adequate quantity of PBSC for transplantation, PBSC must be collected when the number of PBSC has sufficiently increased.

Then, the patient is subjected to a chemoradiation therapy of proper dosage to destroy the bone marrow. Thereafter, the previously collected PBSC are transplanted into the patient so as to rapidly restore hematopoietic function.

A method of detecting PBSC in peripheral blood has been previously reported (U.S. Pat. No. 5,830,701). The hematopoietic progenitor cells (HPC) described in this publication are collectively cells in the pre-blast differentiation stage among cells differentiating from multipotential stem cells to blood cells of various systems. HPC exist in the peripheral blood and are generically PBSC. Accordingly, HPC and PBSC are identical cells. By this method, it is possible to react blood with a reagent (U.S. Pat. No. 5,413,938) capable of detecting immature cells so as to detect and/or count only HPC without using immunological techniques.

The detection of HPC by this method, however, is subject to wide variation in analysis results when there is even a slight change in temperature.

When sample and reagent are reacted at higher than normal temperatures, conventional analyzers minimize changes in analysis results due to temperature fluctuations by reacting the sample after heating the reagent solution to a predetermined temperature by a heating mechanism.

However, when the environmental temperature is somewhat lower than an ideally suitable reaction temperature, flow path temperature is also lowered. Accordingly, when the reagent solution is supplied from a reagent solution supply mechanism to a detecting mechanism, the temperature of the reagent solution is reduced through contact with the flow path. As a result, the reaction required for analysis does not proceed satisfactorily, thus causing variation in the analysis results for the sample.

SUMMARY

The scope of the present invention is defined solely by the appended claims, and is not affected to any degree by the statements within this summary.

A first analyzer embodying features of the present invention includes a heater for heating a fluid; a detector for detecting a signal from an analyte; a flow path connecting the heater and the detector; a fluid supplier for supplying the fluid heated by the heater through the flow path to the detector; a first thermometer for measuring a fluid temperature of the fluid in at least one of the detector and the flow path; and a controller for controlling the heater, the detector, the fluid supplier, and the first thermometer, and for outputting results of an analysis of the signal detected. The controller controls the fluid supplier based on a temperature measured by the first thermometer.

A second analyzer embodying features of the present invention includes a detector for detecting a signal from an analyte; a heater for heating a fluid supplied to the detector; a fluid supplier for supplying the fluid heated by the heater to the detector; and a controller for controlling the detector, the heater, and the fluid supplier, and for outputting an analysis result from the signal detected by the detector. The controller controls the fluid supplier such that heated fluid is supplied to the detector until a temperature of the fluid in the detector attains a predetermined temperature.

A method for analyzing an analyte embodying features of the present invention includes (a) heating a fluid; (b) supplying the fluid to a detector; (c) measuring a temperature of the fluid supplied to the detector; (d) supplying the fluid to the detector until the temperature of the fluid attains a predetermined temperature; (e) supplying the analyte to the detector; (f) detecting a signal from the analyte supplied to the detector; and (g) outputting a result of an analysis of the signal detected.

DETAILED DESCRIPTION OF THE PRESENTLY PREFERRED EMBODIMENTS

The present invention is described hereinafter based on the embodiments shown in the accompanying drawings. This description should not be considered to limit the invention in any way.

The present invention eliminates the previously described problems by controlling a fluid supply mechanism based on the fluid temperature and environmental temperature.

Figure 1:
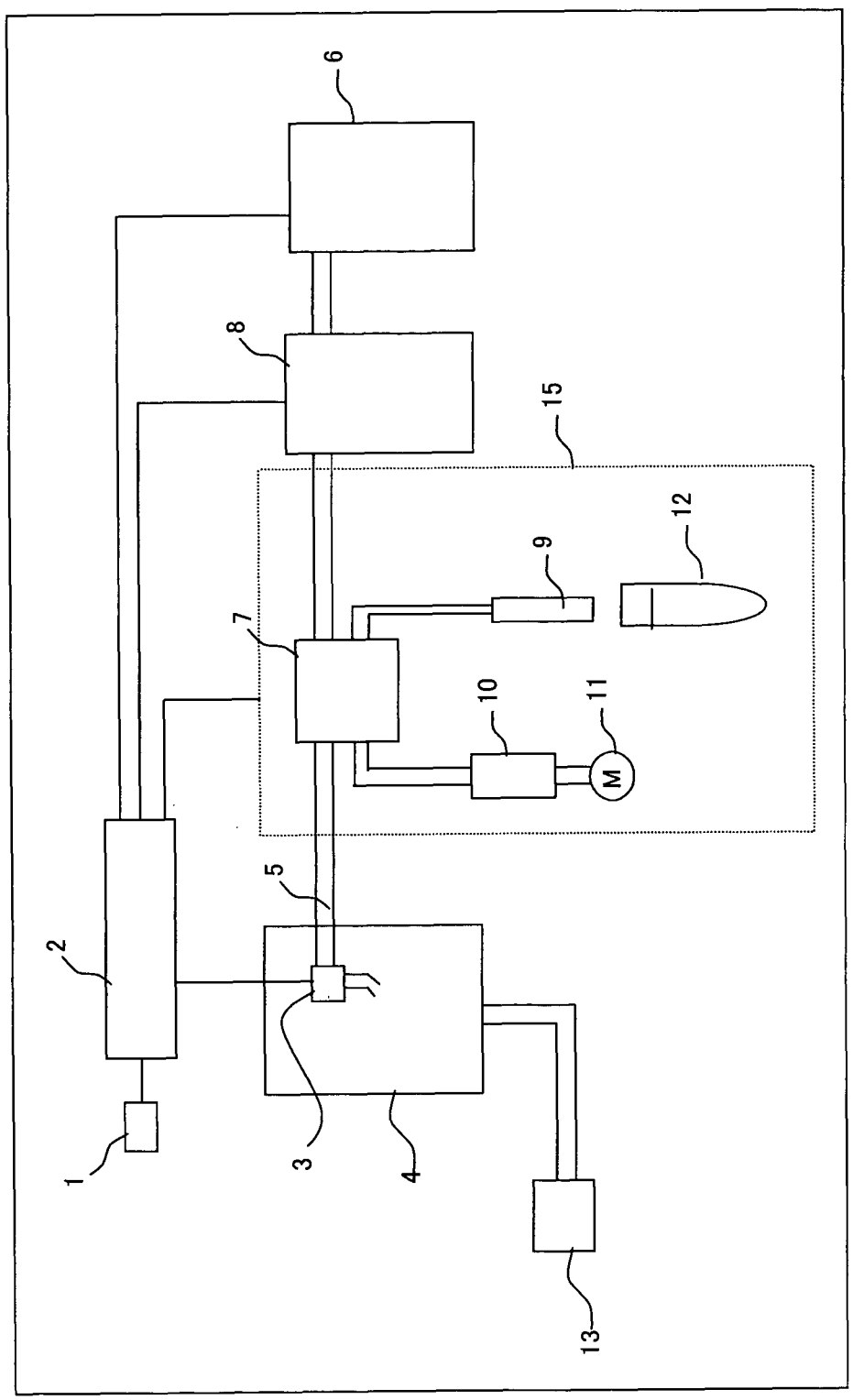
FIG. 1 is a block diagram showing an overview of a sample analyzer embodying features of the present invention.

An overview of a sample analyzer embodying features of the present invention is briefly described below based on the block diagram shown in FIG. 1.

The sample analyzer of the present invention is provided with a reagent fluid supply part 6, heating means 8, analysis part 4, flow path 5, sample supply part 15 (including, for example, a sampling valve 7, pipette 9, syringe 10, and motor 11), environmental temperature measuring means 1, fluid temperature measuring means 3, and operation controller 2. The analysis part 4 and heating means 8 are connected by a flow path 5, such that heated reagent fluid is supplied to the analysis part 4 through the flow path 5.

The sample supply part 15 may be connected in the flow path 5 at a suitable location, or may be constructed so as to supply sample directly to the analysis part 4.

The environmental temperature measuring means 1 is used to measure the temperature in the vicinity of the apparatus, and may be disposed, not only outside the device, but also within the device insofar as it is installed at a location which is not affected by the heat generated by the heater and the like.

The fluid temperature measuring means 3 is used to measure the temperature of the reagent fluid, and may, for example, be disposed within the analysis part 4 or within the flow path 5 near the entrance to the analysis part 4.

The environmental temperature measuring means 1 and the fluid temperature measuring means 3 are respectively connected to the operation controller 2 by circuits. The temperatures measured by the environmental temperature measuring means 1 and the fluid temperature measuring means 3 are input to the operation controller 2.

The reagent fluid supply part 6 is connected to the operation controller 2 by a circuit. When the operation controller issues a command to supply reagent fluid based on the environmental temperature and fluid temperature data, the reagent fluid supply part 6 sends reagent fluid to the analysis part 4 through the flow path 5.

The heating means 8 is connected to the operation controller 2 by a circuit. The operation controller 2 controls the heating means 8, such that the temperature of the reagent fluid attains a predetermined temperature.

The sample supply part 15 includes, for example, a sampling valve 7, pipette 9, syringe 10, and motor 11. The motor 11 operates to collect a fixed amount of sample from a sample vessel 12 by the pipette 9 through the syringe 10, and the sample is supplied to the sample valve 7. This operation is controlled by the operation controller 2 connected by a circuit.

In the following description, a hemocytometer is used as a representative and non-limiting example of a sample analyzer embodying features of the present invention.

Figure 2:
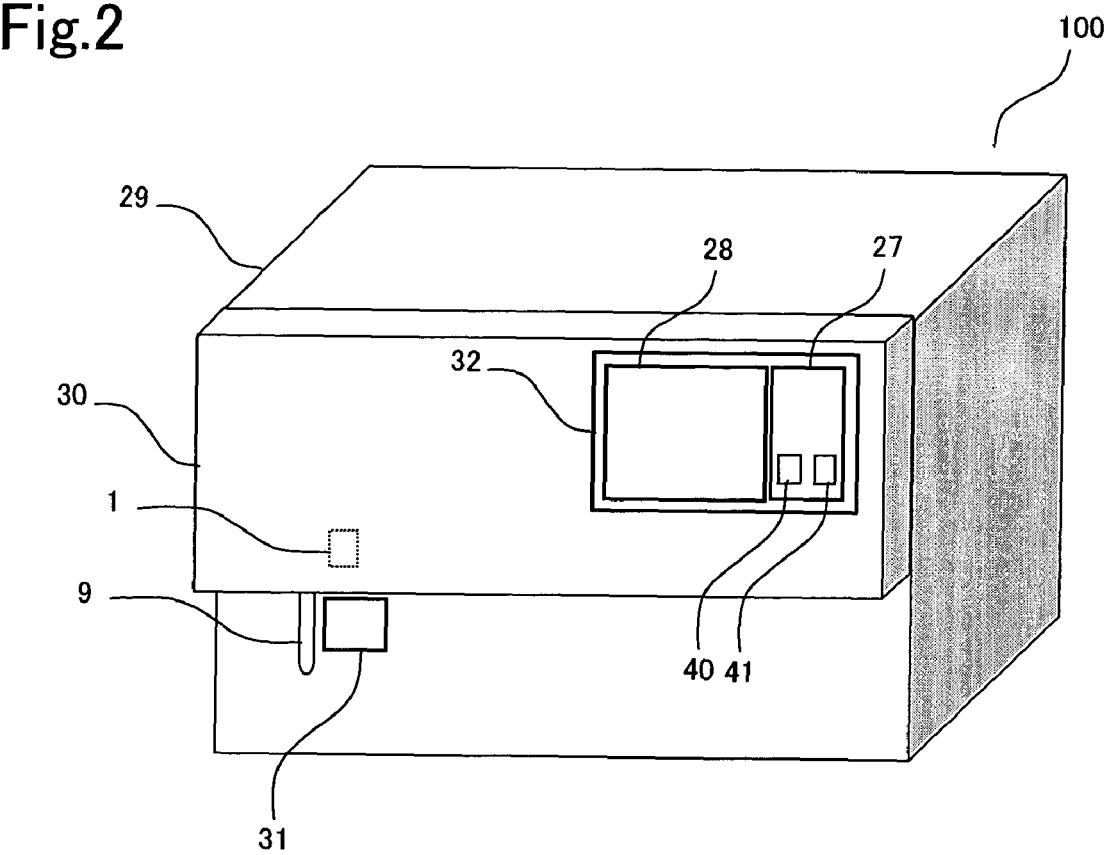
FIG. 2 is a perspective view of a hemocytometer embodying features of the present invention.

FIG. 2 shows a perspective view of a hemocytometer embodying features of the present invention. The hemocytometer 100 is an example of the sample analyzer shown in FIG. 1. Accordingly, parts in common with FIG. 1 are labeled by the same reference numbers shown in FIG. 1.

The hemocytometer 100 includes a body 29 and a front cover 30. This embodiment of the hemocytometer 100 detects HPC.

The body 29 is provided with a pipette 9 for suctioning blood, start switch 31 used for starting analysis and the like, keyboard 27 for receiving input information from a user, and a liquid crystal display 28 for displaying information.

The keyboard 27 is provided with a normal mode key 40 for selecting a normal mode and an HPC mode key 41 for selecting the HPC mode. The normal mode is a mode for calculating the number of leukocytes, erythrocytes and the like, and the HPC mode is a mode for calculating the number of HPC by adding the number of leukocytes and the number of erythrocytes and the like. A user selects the normal mode from the normal mode key 40, and selects the HPC mode from the HPC mode key 41.

The front cover 30 has a window 32, which opens so that the liquid crystal display 28 is visible and to allow operation of the keyboard 27. On the reverse side of the front cover 30 is mounted a thermistor 1 for measuring the environmental temperature.

The environmental temperature is the temperature in the vicinity of the analyzer, and may be the temperature within the analyzer or the temperature outside the analyzer insofar as the location is unaffected by heat generated by the heaters and the like within the analyzer. Accordingly, the thermistor 1 may be mounted within the body 29, or may be mounted on the outside of the body 29 or the front cover 30. Furthermore, the thermistor 1 also may be mounted on a table or wall near the installation location of the hemocytometer 100.

Figure 3:
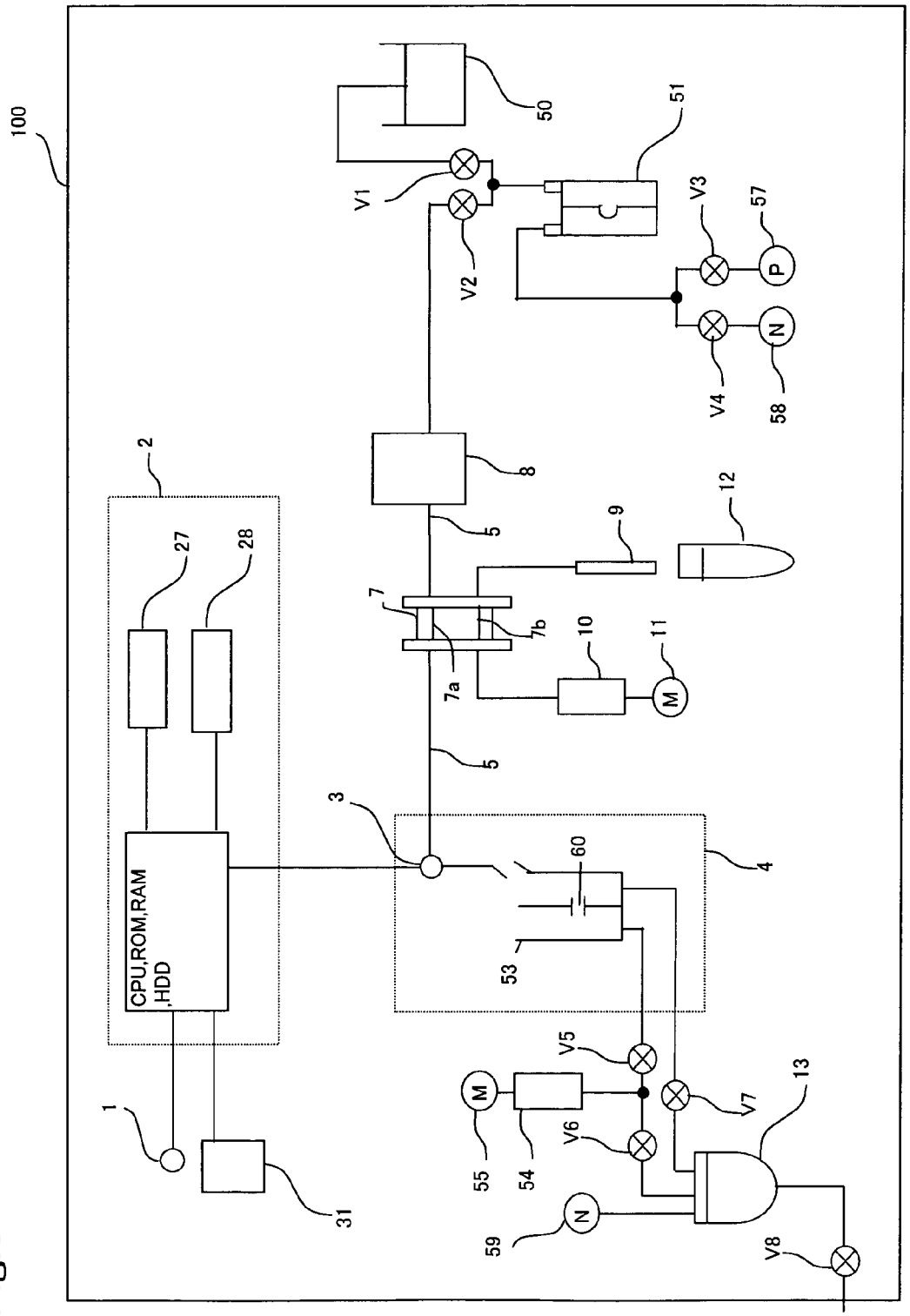
FIG. 3 is an illustration showing the structure of hemocytometer 100.

FIG. 3 shows the structure of the hemocytometer 100. The hemocytometer 100 includes valves V1, V2, V3, V4, V5, V6, V7, and V8 for opening and closing the flow paths, start button 31, reagent chamber 50 for accommodating reagent, diaphragm pump 51 for suctioning and discharging predetermined amounts of fluids, fluid heater 8 for heating fluids to predetermined temperatures, pipette 9 for suctioning blood from the sample vessel 12, syringe 10, motor 11, sampling valve 7 for providing a predetermined amount of blood, detection mechanism 4 for detecting HPC and covering the sensor 53, syringe 54 for suctioning predetermined amounts of sample and reagent fluid from the sensor 53, motor 55, waste fluid chamber 13 for accommodating discard fluid, flow paths connecting various parts, positive pressure source 57 for supplying a positive pressure to the flow paths, and negative pressure sources 58, 59 and the like for supplying a negative pressure to the flow paths.

The sensor 53 is covered by a cover to eliminate the influence of electrical noise, and forms part of the detection mechanism 4.

A thermistor 3 is provided in the flow path 5 within the detection mechanism 4 to measure the temperature of the fluids passing within the flow path 5. The thermistor 3 is connected to the operation controller 2. The operation controller 2 is connected to the thermistor 1 for measuring the temperature of the air in the vicinity of the analyzer, and includes the keyboard 27 and liquid crystal display 28.

The reagent chamber 50, valves V1 and V2, diaphragm pump 51, positive pressure source 57, negative pressure source 58, and the connecting flow paths form the reagent fluid supply mechanism 6. The pipette 9, syringe 10, motor 11, sampling valve 7, and the connecting flow paths form the sample supply mechanism 15.

The hemocytometer 100 is described in detail below with reference to FIG. 4.

Figure 4:
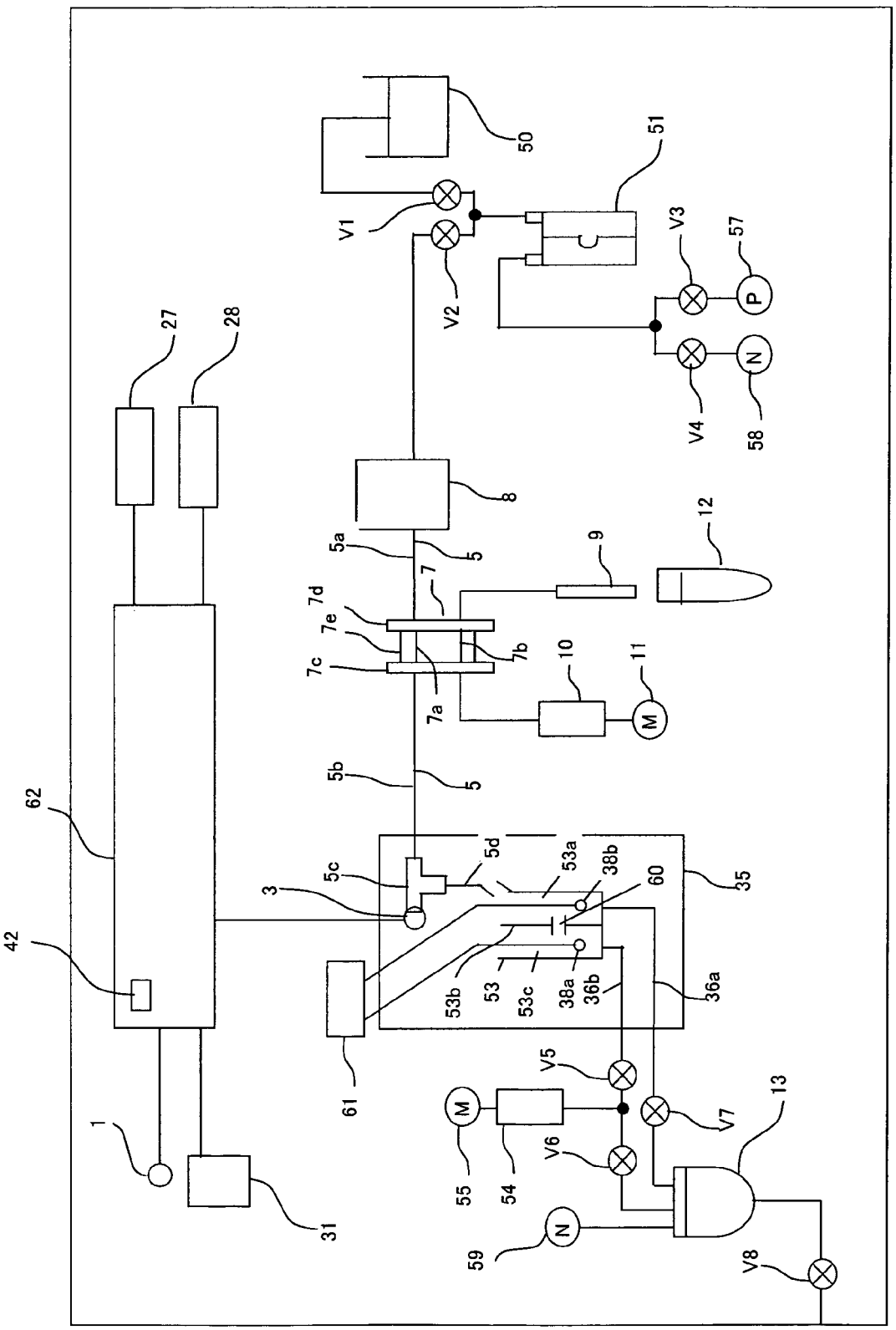
FIG. 4 is an illustration showing the structure of the hemocytometer 100.

FIG. 4 shows the structure of the hemocytometer 100. The hemocytometer 100 is provided with a reagent fluid supply mechanism 6, fluid heater 8, sample supply mechanism 15, detection mechanism 4, flow path 5, thermistor 1, start switch 31, controller 62, keyboard 27, liquid crystal display 28, valves V5 through V8, waste fluid chamber 13, syringe 54, motor 55, and negative pressure source 59.

The reagent fluid supply mechanism 6 is provided with a reagent chamber 50, valves V1 through V4, diaphragm pump 51, positive pressure source 57, negative pressure source 58, and the respective connecting tubes. The valve V2 is connected to the fluid heater 8 through a tube. The reagent fluid supply mechanism 6 receives instructions from the controller 2 and sends out reagent fluid to the detection mechanism 4 through the fluid heater 8 and the flow path 5 and the like.

The reagent chamber 50 internally accommodates reagent fluid such as dilution fluid, stain fluid, hemolytic agent and the like. In the present embodiment, immature leukocyte information (IMI) reagent (see,for example, U.S. Pat. No. 5,413,938) is used as a reagent fluid. The valves V1 through V4 open and close the flow paths. The positive pressure source 57 supplies a positive pressure to the diaphragm pump 51. The negative pressure source 58 supplies a negative pressure to the diaphragm pump 51. The diaphragm pump 51 suctions a predetermined amount of reagent from the reagent chamber 50 and discharges this reagent to the flow path 5 by means of the pressure forces from the positive pressure source 57 and the negative pressure source 58.

A syringe and motor may also be used instead of the diaphragm pump 51, positive pressure source 57 and negative pressure source 58.

The fluid heater 8 heats the reagent fluid to a predetermined temperature via the control of the controller 2.

By way of example, the apparatus for regulating liquid temperature disclosed in U.S. Pat. No. 5,387,334 may be used as the fluid heater 8. The reagent fluid is heated to a predetermined temperature by the fluid heater. 8. This temperature is set to a suitable reaction temperature in accordance with the type of reagent fluid used. In the case of the immature leukocyte information (IMI) reagent used in the present embodiment, the temperature is set between 32.5 and 40° C.

The sample supply mechanism 15 is provided with a pipette 9, syringe 10, motor 11, sampling valve 7, and the respective connecting tubes. When the motor 11 is operated, the syringe 10 operates continuously. By means of this operation, the pipette 9 suctions a fixed amount of blood from the sample vessel 12, and supplies the blood to the sampling valve 7. These operations are controlled by the controller 2.

The sampling valve 7 measures a fixed amount of blood. The sampling valve 7 is formed by stationary valves 7c and 7d, and a movable valve 7e disposed medially to the stationary valves 7c and 7d. The movable valve 7e is provided with blood metered-quantity flow paths 7a and 7b. The sampling valve 7 is inserted in the path of the flow path 5.

A peristaltic pump may be used instead of the sampling valve 7.

The sample supply mechanism 15 need not be inserted in the flow path 5. In this instance, the sample supply mechanism 15 may be constructed such that the pipette 9 is moved to the detection mechanism 4 by a motor so as to supply blood from the pipette 9 to the detection mechanism 4 through the operation of a pump.

The detection mechanism 4 has the function of obtaining an electrical signal from the sample, processing the electrical signal, and transmitting the processed electrical signal to the controller 2 so as to detect leukocytes, HPC or the like. The detection mechanism 4 is provided with part of the flow path 5, part of the tube 36a, part of the tube 36b, sensor 53, current supply circuit 61, electrodes 38a and 38b, thermistor 3, and cover 35. The part of the flow path 5, part of the tube 36a, part of the tube 36b, sensor 53, current supply circuit 61, electrodes 38a and 38b, and thermistor 3 are covered by the cover 35. The cover 35 is provided to eliminate the influence of electrical noise.

The sensor 53 is formed by a chamber 53a, chamber 53c, and a partition 53b disposed between the chambers. Micropore 60 is provided in the partition 53b. The fluid within the chamber 53a is allowed to move to the chamber 53c by passing through the pores of the partition 53b.

Tubes 36a and 36b are connected at the bottom of the chambers 53a and 53c, respectively. The tubes 36a and 36b are flow paths for fluids discharged from the chambers 53a and 53c, respectively.

The electrodes 38a and 38b are mounted within the interiors of the chambers 53a and 53c, respectively. The electrodes 38a and 38b are connected to a current supply circuit 61.

The current supply circuit 61 supplies an electrical current which flows to the electrodes 38a and 38b. The current supply circuit 61 measures the voltage and capacitance between the electrodes 38a and 38b, processes the values thus obtained, and transmits these processed values to the controller 2.

The thermistor 3 is provided to measure the temperature of fluids flowing in the flow path 5. The thermistor 3 is connected to the controller 2.

A detection mechanism capable of analyzing a plurality of cellular information may be provided in the particle analyzer as the detection mechanism 4. Well known flow cytometers used as optical detection mechanisms, and detection mechanisms employing an RF/DF detection method used as electrical resistance type detection mechanism, may be used as the above-mentioned detection mechanism. For HPC detection, it is desirable to use a detection mechanism employing an RF/DF detection method, for example, a detection method such as model XE-2100 (Sysmex K.K.).

Information on the size of cells, information on cell morphology, and intracellular information are included in cell information. Information such as DC signal and low angle scattered light intensity information, and the like, may provide information on cell size and cell morphology. A DC signal is a signal based on the difference in electrical resistance of a cell that is generated when a cell passes through a micropore to which flows a direct electrical current. Low angle scattered light is the scattered light found at 1 to 6° relative to an optical axis.

Intracellular information may be information such as an RF signal, intensity of anterior high-angle scattered light, intensity of lateral scattered light, intensity of posterior scattered light, deflected resolution and the like. The RF signal is a signal based on the permittivity of a cell that is generated when a cell passes through a micropore to which a high frequency current flows. Anterior high-angle scattered light is scattered light at 8 to 20° relative to an optical axis. Lateral scattered light is scattered light at 70 to 110° relative to an optical axis. Posterior scattered light is scattered light at 120 to 180° relative to an optical axis.

The flow path 5 is a flow path from the fluid heater 8 to the sensor 53. Within the flow path 5 flows a fluid heated by the fluid heater 8. The flow path 5 is formed by tubes 5a and 5b, T section 5c, and nozzle 5d. A reagent fluid is normally accommodated in the flow path 5.

The tube 5a connects the fluid heater 8 and the stationary valve 7d.

One end of the tube 5b is connected to the stationary valve 7c. The T section 5c is connected to the other end of the tube 5b. The T section 5c is positioned inside the cover 35. The nozzle 5d is connected to the T section 5c. The nozzle 5d is disposed at the top of the chamber 53a so as to inject reagent fluid into the interior of the chamber 53a.

The reagent fluid sent from the fluid heater 8 is injected to the sensor 53 through the tube 5a, stationary valve 7d, blood metered-quantity flow path 7a, stationary valve 7c, tube 5b, T section 5c, and nozzle 5d.

Although the tubes 5a and 5b are formed of resin material, they may also be formed of metal. A flow path having a channel may also be used instead of the tubes 5a and 5b. The lengths of the tubes 5a and 5b are not limited.

The thermistor 3 is mounted at the T section 5c. The thermistor 3 is mounted in a position so as to come into contact with the reagent fluid passing within the T section 5c.

Furthermore, the thermistor 3 may also be attached within the sensor 53, to the tube 5a, tube 5b, or nozzle 5d. The thermistor 3 is a thermometer for measuring the temperature of the reagent fluid heated by the fluid heater 8. The thermistor 3 is desirably mounted at a position within the detection mechanism 4 or near the detection mechanism 4.

A thermocouple also may be used as the thermometer instead of the thermistor 3.

The blood suctioned by the pipette 9 is mixed within the sensor 53 with the reagent fluid transported by the reagent fluid supply mechanism 6.

The hemocytometer 100 may also be constructed so as to mix blood and reagent within the flow path 5. The hemocytometer 100 may also be provided with another mixing vessel and constructed so as to mix the blood and reagent within this mixing vessel.

When the blood and reagent are mixed, components contained in the blood react with the reagent. In the present embodiment, erythrocytes in the blood react with the previously mentioned IMI reagent fluid, and hemolysis results. Furthermore, leukocytes other than immature leukocytes have cytoplasm removed and reduced.

The valves V5 through V8 open and close the flow paths. The valves V5 through V8 close the flow paths in the initial state.

When the valve V5 is open, the syringe 54 suctions a predetermined amount of blood and reagent from within the chamber 53a through the micropore 60, chamber 53c and tube 36b. Furthermore, when the valve V6 is closed, the syringe 54 discharges discard fluid to the waste fluid chamber 13.

The waste fluid chamber 13 accommodates discard fluid discharged from the chambers 53a and 53c. The negative pressure source 59 supplies a negative pressure to the waste fluid chamber 13.

The valve V8 is open when discard fluid accommodated in the waste fluid chamber 13 is discharged outside the apparatus.

The thermistor 1 is connected to the controller 62. As previously mentioned, the thermistor 1 measures the environmental temperature.

The start switch 31 is connected to the controller 62.

The controller 62 includes a CPU at its core, ROM, RAM used as a work area, and a hard disk for storing data and applications. The controller 62 is provided with a timer 42. The controller 62 receives the temperatures measured by the thermistors 1 and 3. The controller 62 issues operation instructions to the reagent fluid supply mechanism 6 based on the temperatures received from the thermistors 1 and 3. The controller 62 is connected to the keyboard 27 and the liquid crystal display 28.

The controller 62, keyboard 27, and liquid crystal display 28 form the operation controller 2 (FIG. 3). A commercial personal computer with Windows 2000 (Windows is a registered trademark of Microsoft Corporation) installed as an operating system may also be used as the operation controller 2.

The operation of the hemocytometer 100 is described below.

Figure 5:
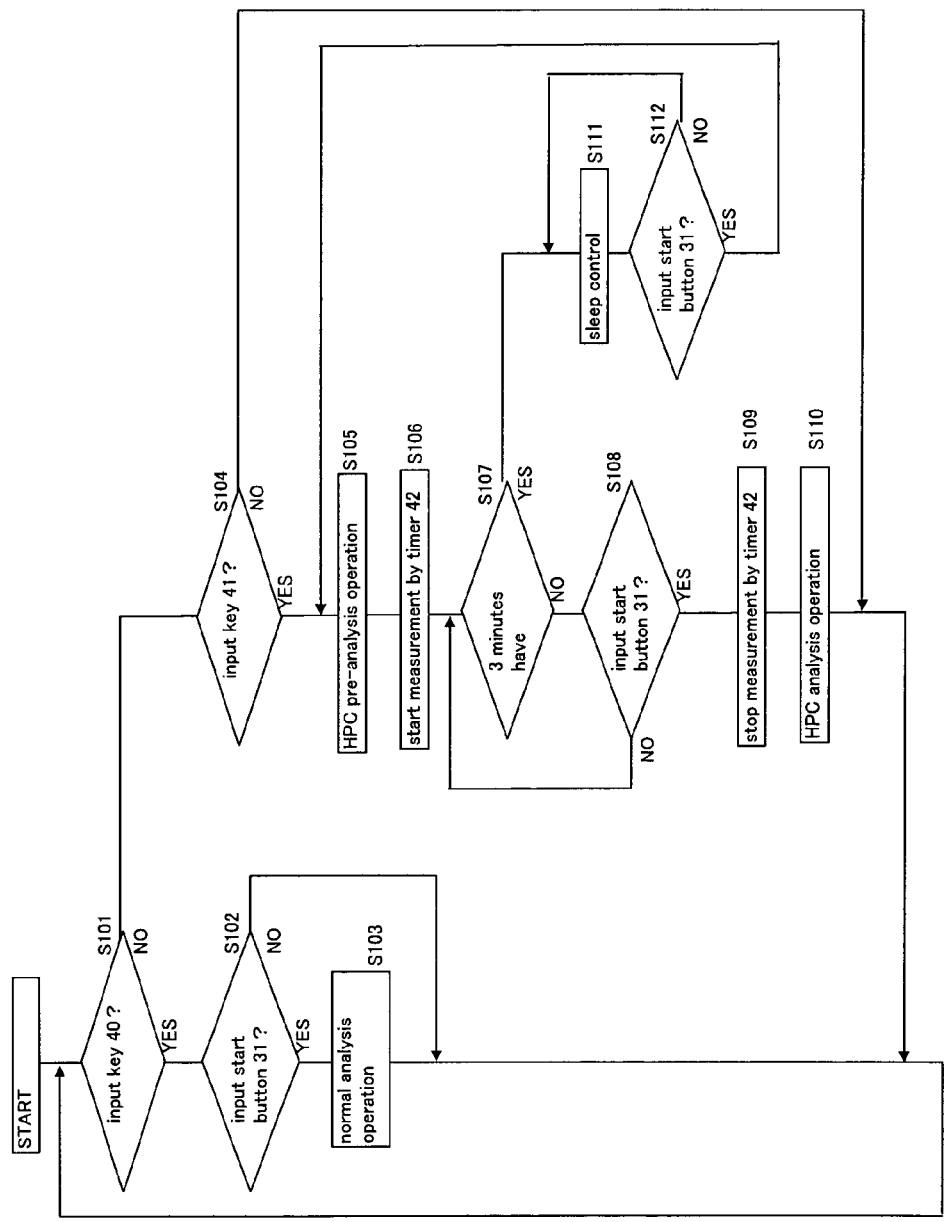
FIG. 5 is a flow chart outlining the general processing sequence of the controller 2.

FIG. 5 is a flow chart showing an overview of the processing sequence in controller 2.

In S101, processing is executed to determine whether or not there is input from the normal mode key 40. If there is input from the normal mode key 40, the routine continues to S102. When there is no input from the normal mode key 40, the routine advances to S104.

In S102, processing is executed to determine whether or not there is input from the start button 31. If there is input from the start button 31, the routine continues to S103. When there is no input from the start button 31, the routine continues to S101. In S103, processing is executed to control normal analysis operation. Normal analysis operation includes suctioning blood, processing the blood, and calculating the analysis result (the number of HPC is not included in the analysis result).

In S104, processing is executed to determine whether or not there is input from the HPC mode key 41. If there is input from the HPC mode key 41, the routine continues to S105. When there is no input from the HPC mode key 41, the routine continues to S101.

Figure 6:
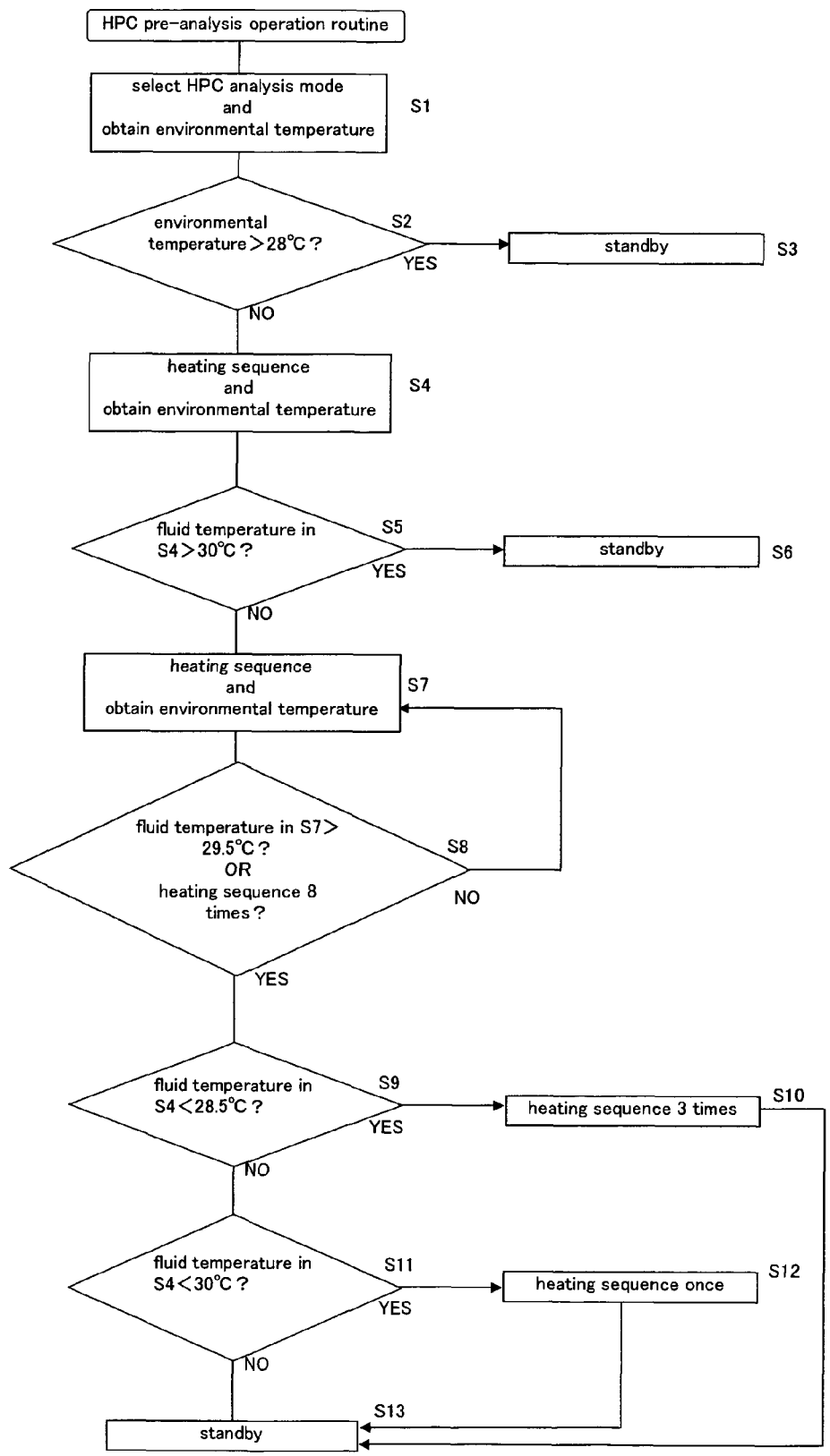
FIG. 6 is a flow chart showing the processing executed in S105.

In S105, controls are executed to control the HPC pre-analysis operation. Details of S105 are shown in FIG. 6.

In S106, processing is executed to start measurements by the timer 42.

In S107, processing is executed to determine whether or not 3 minutes have elapsed since the start of the measurement by the timer 42. If 3 minutes have elapsed, the routine advances to S111. When 3 minutes have not elapsed, the routine continues to S108.

In S108, processing is executed to determine whether or not there is input from the start button 31. If there is input from the start button 31, the routine continues to S109. When there is no input from the start button 31, the routine continues to S107.

In S109, processing is executed to stop the measurement by the timer 42.

Figure 7:
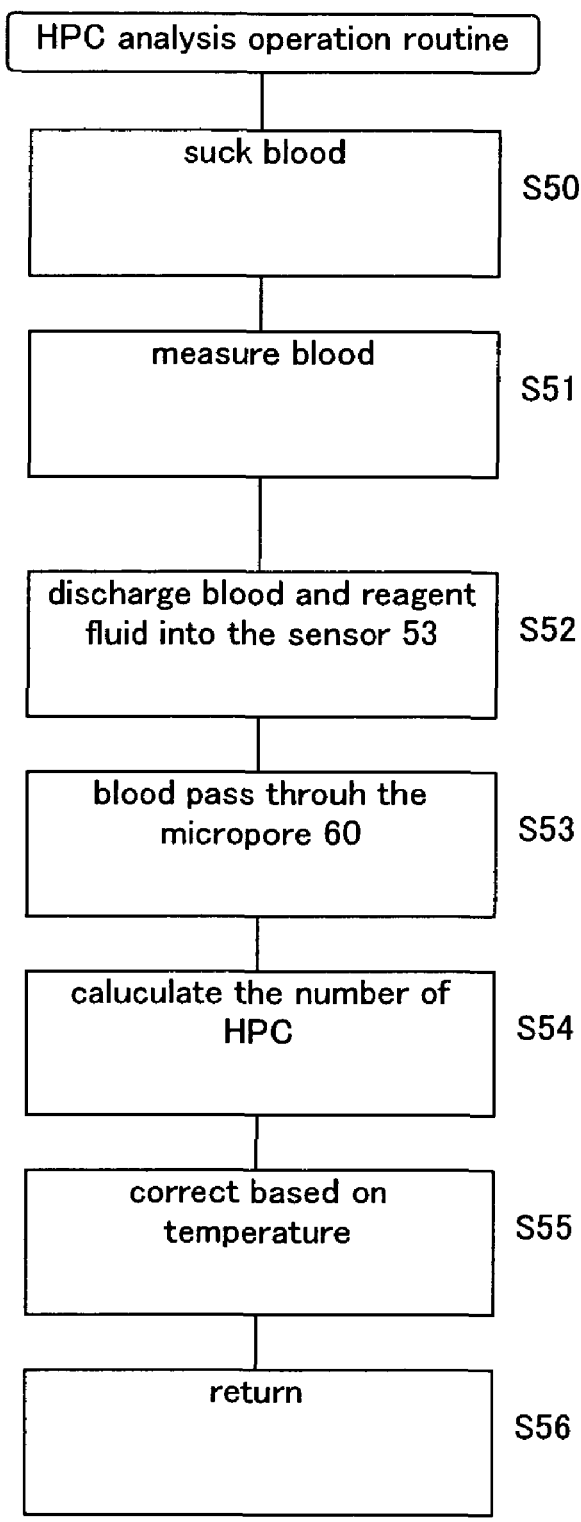
FIG. 7 is a flow chart showing the processing executed in S110.

In S110, processing is executed to control the HPC analysis operation. Details of S110 are shown in FIG. 7.

In S111, a sleep control process is executed. When this process is executed, the hemocytometer 100 enters a power saving mode to reduce power consumption, and enters a state wherein each mechanism is stopped until there is input from the start button 31.

In S112, processing is executed to determine whether or not there is input from the start button 31. If there is input from the start button 31, the routine continues to S105. When there is no input from the start button 31, the routine continues to S111.

Details of S105 are described below with reference to FIG. 6. FIG. 6 is a flow chart illustrating the process executed in S105.

When a user selects the HPC analysis mode from the keyboard 27, the environmental temperature is obtained by the thermistor 1 (S1). The hemocytometer 100 can be operated under a mode which performs analysis of HPC and under a mode which does not perform analysis of HPC; the mode which performs analysis of HPC is called the HPC analysis mode. When the environmental temperature obtained by the thermistor 1 is 28° C. or higher, the hemocytometer 100 enters a standby state (hereinafter, the state wherein HPC analysis is possible is referred to as the "standby" state), and enters a state wherein sample blood can be suctioned (S2, S3). When the environmental temperature is less than 28° C., a heating sequence is executed (S2, S4).

The heating sequence is described below.

Unless specifically mentioned otherwise, valves are closed.

Reagent fluid (the previously mentioned IMI reagent in the present embodiment) is retained in the fluid heater 8 beforehand, and is heated to a predetermined temperature.

When the valves V1 and V4 are opened, a predetermined amount of reagent fluid is suctioned into the diaphragm pump 51 by the negative pressure source 58.

When the valves V1 and V4 are closed and the valves V2 and V3 are opened, the predetermined amount of reagent fluid in the diaphragm pump 51 is injected in a direction toward the fluid heater 8 by the positive pressure source 57. In this way, the reagent fluid retained beforehand in the fluid heater 8 is suctioned therefrom, and the reagent fluid passes through the flow path to the sensor 53. At this time, the temperature of the reagent fluid is measured in real time by the thermistor 3.

When the valves V2 and V3 are closed, the reagent fluid within the sensor 53 is discharged to the waste chamber 13 by opening the valve V7. Thereafter, the valve 7 is closed and the heating sequence ends. By executing the heating sequence, the flow path 5 and the sensor 53 are heated, and the fluid temperature is measured by the thermistor 3.

The process executed in S105 is described below.

When the temperature of the reagent fluid (i.e., the maximum temperature among the fluid temperatures measured in real time, and similarly hereafter) measured by the thermistor 3 in the heating sequence in S4 is 30° C. or higher, the hemocytometer 100 enters standby, a state wherein sample blood can be suctioned (S5, S6).

When the reagent temperature measured by the thermistor 3 in the heating sequence in S4 is less than 30° C., the temperature of the reagent fluid is measured by again executing the heating sequence (S5 and S7).

When the temperature of the reagent fluid measured in S7 is less than 29.5° C., the reagent fluid temperature is measured by again executing the heating sequence (S8, S7).

When the temperature of reagent fluid measured in S7 is greater than 29.5° C., and when the temperature of the reagent fluid measured in S4 is less than 28.5° C. (S8, S9), the heating sequence is executed 3 times (S10), and the hemocytometer 100 enters standby (S13).

When the temperature of the reagent fluid measured in S7 is greater than 29.5° C., and when the temperature of the reagent fluid in S4 is equal to or greater than 28.5° C. (S9) but less than 30.0° C. (S11), the heating sequence is executed once (S12), and the hemocytometer 100 enters standby (S13).

When the heating sequence has been executed 8 times and the temperature of the reagent fluid is less than 29.5° C., the operations in S9 and below are executed in the same manner as previously described.

The preparation for HPC analysis described above ends, and it is possible to suction blood.

Details of S110 are described below with reference to FIG. 7. FIG. 7 is a flow chart showing the process executed in S110. For convenience, only key operations are described, and a description of the cleaning operation is omitted.

A predetermined amount of blood is suctioned from the sample vessel 12 through the pipette 9 by the suction operation of the syringe 10 and the operation of the motor 11. In this way, blood fills the blood metered-quantity flow path 7a of the sample valve 7 (S50).

The blood is measured via the rotation of the movable valve of the sampling valve 7 (S51).

The valves V1 and V4 are opened, and a predetermined amount of reagent fluid is suctioned into the diaphragm pump 51 (S52).

The valves V1 and V4 are closed, the valves V2 and V3 are opened, and the reagent fluid within the diaphragm pump 51 is discharged in the direction of the fluid heater 8. In this way, reagent fluid retained within the flow path beforehand and a metered quantity of blood measured in S51 are discharged into the sensor 53 (S52). Furthermore, in S52, the temperature of the reagent fluid flowing within the flow path 5 is measured by the thermistor 3.

The valves V6 and V7 are closed and the valve V5 is opened, to induce a suctioning operation of a predetermined quantity by the syringe 54. In this way, blood passes through the micropore 60 of the sensor 53, and the change in voltage is detected at this time (S53). In this way, a two-dimensional distribution (scattergram) is obtained (RF/DC detection method). The number of HPC is calculated from this scattergram (S54). The method for calculating the number of HPC is described in detail in U.S. Pat. No. 5,830,701, which is hereby incorporated by reference in its entirety except that in the event of any inconsistent disclosure or definition from the present application, the disclosure or definition herein shall be deemed to prevail.

In S55, processing is executed to correct the number of HPC calculated in S54 based on the temperature obtained in S52. The process executed in S55 is described below.

Figure 8:
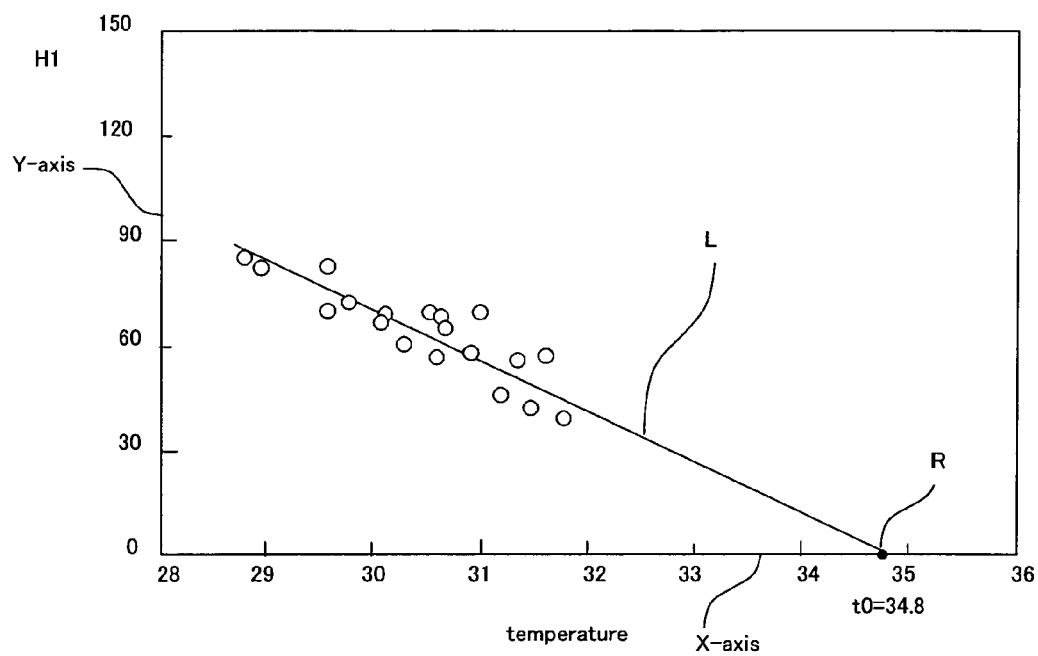
FIG. 8 is a graph showing the relationship between temperature and number of HPC before correction.
Figure 9:
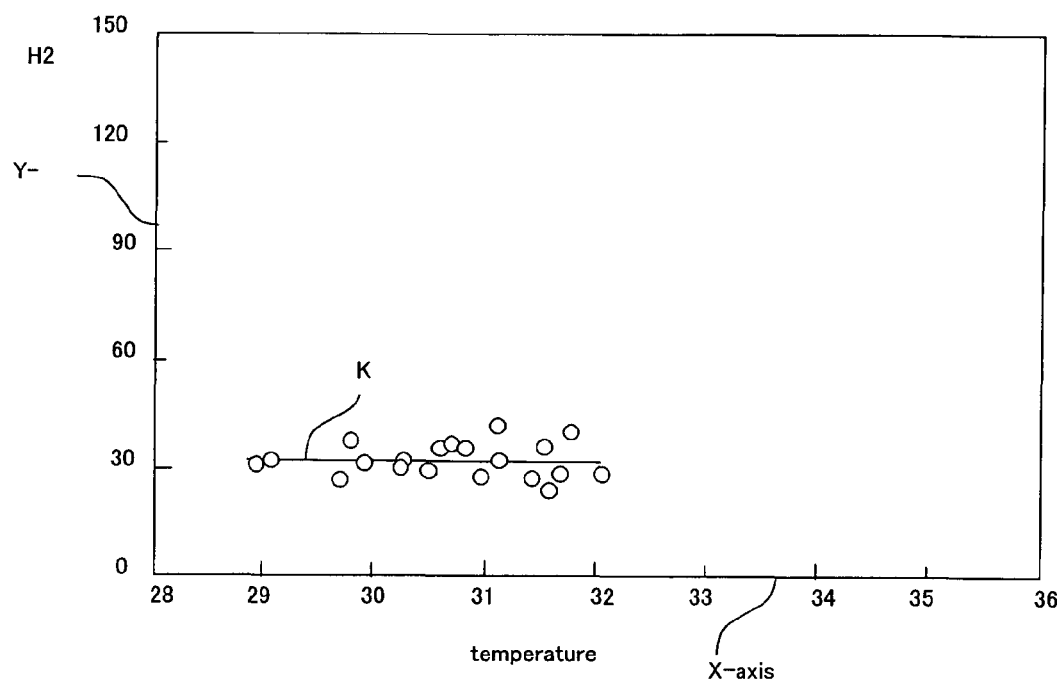
FIG. 9 is a graph showing the relationship between temperature and number of HPC after correction.

The correction can be accomplished using equation (1) below $$H2 = \frac{H1}{t1 - t0} * a - \frac{H1 * t0}{t1 - t0}$$

wherein "H2" represents the number of HPC after correction, "a" represents the optimum reaction temperature, "H1" represents the number of HPC before correction, "t0" represents the X-axis intersection, and "t1" represents the fluid temperature obtained by the fluid temperature measuring means during the reaction of the IMI reagent. In the equation, "t0" is determined in the following manner. The numbers of HPC before correction are set on the Y-axis, and the fluid temperatures obtained by the fluid temperature measuring means are set on the X-axis. The intersection of the X-axis and a straight line obtained by plotting a plurality of analysis values in the graph is designated t0. FIG. 8 is a graph showing the relationship between the fluid temperature and the number of HPC before correction, and FIG. 9 is a graph showing the relationship between the fluid temperature and the number of HPC after correction. In the graph shown in FIG. 8, t0=34.8° C. It can be understood from the graph in FIG. 9 that the correction using equation (1) produces a suitable number of HPC.

More specifically, the correction may be accomplished using equation (2) below $$H2 = \frac{H1 * (32.5 - 34.8)}{t1 - 34.8}$$

wherein "H2" represents the number of HPC after correction, "H1" represents the number of HPC before correction (i.e., the number of HPC obtained in S54), and t1 represents the reagent fluid temperature obtained by the thermistor 3 in S52. Equation (2) introduces a temperature of 32.5° C. as the optimum reaction temperature "a" in equation (1).

The value of t0 can be determined in the following manner. A plurality of blood samples having essentially the same number of HPC are analyzed using IMI reagent fluid of various temperatures. Then, the obtained number of HPC H1 are set on the Y-axis, and the temperatures measured by the thermistor 3 are set on the X-axis, and when the analysis results are graphically plotted, the analysis results align along a certain straight line. The temperature indicated at the intersection of this straight line and the X-axis is designated t0. In the graph shown in FIG. 8, the Y-axis represents H1, the number of HPC before correction, and the X-axis represents the temperature measured by the thermistor 3. The analysis results align along a straight line L. The temperature indicated at the intersection R of the straight line L and the X-axis is the value t0, and in the present embodiment, t0=34.8° C.

In the graph shown in FIG. 9, when the temperature is in the range of approximately 29 to 32° C., the number of HPC H2 align along a line K parallel to the X-axis. That is, the number of HPC H2 is a constant value. This drawing represents a suitable correction in S55.

The above-described HPC analysis operation is completed (S56).

When a predetermined time has elapsed before the suctioning of the next sample, the operations of S1 through S13 shown in FIG. 6 are executed again. When a predetermined time has not elapsed, the routine may start from the operation of S50 since the temperatures in the flow path 5 and sensor 11 will not have changed greatly in such a short time.

Although it is desirable that a reagent fluid is used as the fluid supplied to the analysis part, water and the like may also be used since the fluid supply part of the present invention has the purpose of stabilizing the flow path temperature.

By way of example, a diluent for diluting a sample, a stain for staining a component contained in the sample, hemolytic agent to hemolyze blood components such as erythrocytes, and the like may be used as a reagent fluid.

When a sample and a reagent fluid are mixed, the reagent fluid reacts with a component contained in the sample depending on the sample and type of reagent. For example, when the sample is blood, and the reagent is an IMI reagent, the erythrocytes in the blood are hemolyzed by the reaction, and leukocytes other than pre-blast cells have cytoplasm removed and reduced.

The first predetermined value is a temperature selected so as to not reduce the temperature of the fluid passing through the flow path, which arises when the environmental temperature is less than the temperature of the fluid flowing through the flow path. The first predetermined value can be determined by considering the length and material of the flow path, and the desired reaction temperature of the sample and the reagent. Specifically, when heated fluid is actually supplied and the environmental temperature is at a certain degree Centigrade, a check is made to determine whether the heated fluid is supplied to the analysis part without a decrease in temperature. Such an environmental temperature is standardized as the first predetermined value.

It is desirable that the operation control part compares the temperature of the fluid obtained by the fluid temperature measuring means and a second predetermined value, and when the fluid temperature is less than the second predetermined value, fluid is supplied from the fluid supply part to the analysis part. The temperature of the fluid is measured again by the fluid temperature measuring means, and the supply of fluid from the fluid supply part to the analysis part is stopped when the re-measured fluid temperature exceeds the second predetermined value. Since the flow path and analysis part are adequately warmed if the temperature of the fluid is higher than the second predetermined value, it is unnecessary to supply more fluid. Conversely, since the temperatures of the flow path and analysis part are lower than the temperature of the fluid when the fluid temperature is less than the second predetermined value, it is necessary to supply heated fluid from the fluid supply part to the analysis part to warm the flow path and analysis part. In this way, only a necessary amount of fluid is supplied to the analysis part to attain an optimum temperature of the flow path and the analysis part before a sample is analyzed.

The temperature used as the second predetermined value may be selected so as to be an optimum fluid temperature for sample analysis when the heated fluid arrives at the analysis part. Specifically, a check is made to determine whether or not a desired analysis result is obtained when heated fluid is actually supplied and the fluid temperature obtained by the fluid temperature measuring means is at a certain degree Centigrade. This fluid temperature is standardized as the second predetermined temperature.

It is desirable that analysis by the analysis part is enabled when the operation control part compares the environmental temperature obtained from the environmental temperature measuring means and the first predetermined value and the environmental temperature is higher than the first predetermined value. Likewise, it is desirable that analysis by the analysis part is enabled when the operation control part compares the fluid temperature obtained from the fluid temperature measuring means and the second predetermined value and the fluid temperature is higher than the second predetermined value.

If analysis of a sample is started in this state, analysis can be performed at a desired temperature, and temperature-induced errors can be minimized.

In the sample analyzer of the present invention, the analysis part can be used to analyze materials including but not limited to blood components such as HPC (hematopoietic progenitor cells), PBSC, leukocytes, erythrocytes, and platelets, urine components such as leukocytes, erythrocytes, and microbes, and industrial particles requiring a staining process for measurement. Among these, the sample analyzer of the present invention is particularly useful for analyzing HPC. The reaction optimum temperature range for HPC and a reagent (for example, IMI reagent) desirable for analysis of HPC is extremely narrow because maintaining the IMI reagent at an optimum fluid temperature during the reaction is preferrable for the measurement of HPC.

The present invention can be applied to sample analyzers for analyzing materials including but not limited to blood components such as leukocytes, erythrocytes, and platelets, urine components such as leukocytes, erythrocytes, and microbes, and industrial particles requiring a staining process for measurement.

The sample analyzer of the present invention obtains accurate analysis results by analyzing samples under optimum conditions.

Specifically, by using the minimum of fluid to warm the flow path and sensors, the temperature of the reagent fluid used in analysis is stabilized, and errors in analysis results due to temperature fluctuation are minimized. More accurate analysis results can be obtained by performing temperature correction on the obtained analysis results.

The foregoing detailed description has been provided by way of explanation and illustration, and is not intended to limit the scope of the appended claims. Many variations in the presently preferred embodiments illustrated herein will be obvious to one of ordinary skill in the art, and remain within the scope of the appended claims and their equivalents.

What is claimed is:

1. An analyzer comprising:
a heater for heating a reagent fluid;
a detector configured to interrogate a sample mixed with the reagent fluid which has been heated by the heater, wherein the heater and the detector are arranged at a distance therebetween;
a flow path that runs over the distance between the heater and the detector for delivery of the heated reagent fluid from the heather to the detector;
a fluid supplier configured to flow the heated reagent fluid in the flow path and the detector to adjust a temperature of the flow path and the detector with the heated reagent fluid flown therein;
a first thermometer that measures a fluid temperature of the reagent fluid situated in at least one of the detector and the flow path; and
a controller responsive to the measured fluid temperature to direct the fluid supplier to control a flow of the heated reagent fluid in the flow path and the detector in order to thereby make the detector thermally ready for accurate analysis.

2. The analyzer of claim 1 further comprising a second thermometer that measures an environmental temperature, wherein the controller is also responsive to the measured environmental temperature to direct the fluid supplier.

3. The analyzer of claim 2, wherein the controller directs the fluid supplier to supply the heated reagent fluid to the flow path to heat the flow path if the measured environmental temperature is lower than a threshold value.

4. The analyzer of claim 3, wherein the first thermometer measures the fluid temperature of the reagent fluid in the flow path, and the controller directs the fluid supplier to re-supply the heated reagent fluid to the flow path to heat the flow path if the measured fluid temperature of the reagent fluid in the flow path is lower than a threshold value.

5. The analyzer of claim 1, wherein the first thermometer measures the fluid temperature of the reagent fluid supplied in the flow path, and the controller directs the fluid supplier to supply the heated reagent fluid to the flow path to heat the flow path if the measured fluid temperature of the reagent fluid in the flow path is lower than a threshold value.

6. The analyzer of claim 1, wherein the controller determines, based on the fluid temperature measured by the first thermometer, whether or not the detector is thermally ready to interrogate the sample.

7. The analyzer of claim 2, wherein the controller determines, based on the environmental temperature measured by the second thermometer, whether or not the detector is thermally ready to interrogate the sample.

8. The analyzer of claim 1, wherein the analyzer operates in a first operating mode in which the controller controls the fluid supplier, based on the fluid temperature measured by the first thermometer, and a second operating mode in which the controller controls the fluid supplier , based on the fluid temperature measured by the first thermometer.

9. The analyzer of claim 8, wherein the controller, while the analyzer is in the first operating mode, starts the interrogation of the sample if the measured fluid temperature is equal to or higher than a threshold value, and while the analyzer is in the second operating mode, starts the interrogation regardless of the fluid temperature.

10. The analyzer of claim 1, wherein the controller calibrates the result of the interrogation, using the fluid temperature measured by the first thermometer.

11. The analyzer of claim 1, wherein the analyte is HPC.

12. An analyzer comprising:
a detector configured to interrogate a sample mixed with a reagent fluid;
a heater that heats the reagent fluid to be supplied to the detector, wherein the heater and the detector are arranged at a distance therebetween;
a fluid supplier configured to flow the heated reagent fluid over the distance to deliver the heated reagent fluid to the detector from the heater; and
a controller configured to direct the fluid supplier to control a flow of the heated reagent fluid to the detector in order to make the detector thermally ready for accurate analysis.

13. The analyzer of claim 12 further comprising a first thermometer that measures a temperature of the reagent fluid in the detector;
wherein the controller determines that the temperature of the reagent fluid in the detector has reached a threshold temperature if the fluid temperature of the reagent fluid measured by the first thermometer exceeds the threshold value.

14. The analyzer of claim 12, further comprising a second thermometer that measures an environmental temperature;
wherein the controller determines that the temperature of the reagent fluid in the detector has reached a threshold temperature if the environmental temperature measured by the second thermometer exceeds the threshold value.

15. The analyzer of claim 13, wherein the analyzer operates in a first mode in which the controller controls the fluid supplier to flow the heated reagent fluid into the detector so as to bring up the temperature of the reagent fluid in the detector to the threshold temperature, and operates in a second mode in which the controller controls the fluid supply regardless of the temperature of the reagent fluid.

16. The analyzer of claim 15, further comprising a selector configured to select at least one of the first mode and the second mode;
wherein immediately after the selector selects the first mode, the controller controls the fluid supplier to flow the heated reagent fluid into the detector so as to bring up the temperature of the reagent fluid in the detector to the threshold temperature.

17. The analyzer of claim 13, wherein the controller allows the detector to interrogate the sample during a set time after the temperature of the reagent fluid in the detector reached the threshold temperature.

18. A method for analyzing an analyte in a sample comprising computer executable steps executed by a processor of an analyzer to implement:

(a) heating a reagent fluid by a heater;
(b) supplying the heated reagent fluid to a detector from the heater through a flow path which runs over a distance between the heather and the detector;
(c) measuring a temperature of the reagent fluid in the detector;
(d) supplying any necessary amount of the heated reagent fluid to the detector from the heater through the flow path so that the temperature of the heated reagent fluid in the detector will reach a threshold temperature;
(e) starting to supply the sample into the detector after the temperature of the heated reagent in the detector has reached the threshold temperature; and
(f) starting to interrogate the sample supplied to the detector.

19. The method of claim 18, wherein the steps (a), (b), (c), (d), (e), and (f) are performed in the listed order successively.

20. The method of claim 18, wherein the temperature of the reagent fluid in the detector is measured while the heated reagent fluid is being supplied to the detector.

21. The analyzer of claim 1 further comprising a sample supplier configured to supply the sample to the detector, wherein the sample supplier supplies a sample when the fluid temperature of the reagent fluid measured by the first thermometer has reached a threshold temperature.

22. The analyzer of claim 21, wherein the fluid supplier supplies the heated reagent fluid to the detector so that the fluid temperature of the reagent fluid measured by the first thermometer will reach the threshold temperature; and
wherein the fluid supplier supplies the reagent fluid to the detector after the fluid temperature of the reagent fluid measured by the first thermometer has reached the threshold temperature, and the sample supplier starts to supply the sample to detector when the fluid temperature of the reagent fluid measured by the first thermometer has reached the threshold temperature, so that the ample mixed with the reagent fluid is supplied to the detector.

* * * * *